United States Patent
Goddard

(10) Patent No.: US 8,784,294 B2
(45) Date of Patent: Jul. 22, 2014

(54) SYNTHETIC GRAFT FOR SOFT TISSUE REPAIR

(75) Inventor: James Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 361 days.

(21) Appl. No.: 12/787,204

(22) Filed: May 25, 2010

(65) Prior Publication Data

US 2010/0312043 A1    Dec. 9, 2010

Related U.S. Application Data

(60) Provisional application No. 61/183,654, filed on Jun. 3, 2009.

(51) Int. Cl.
*A61F 2/00* (2006.01)
*A61F 2/02* (2006.01)
*A61F 13/00* (2006.01)

(52) U.S. Cl.
USPC .............................................. 600/30; 600/37

(58) Field of Classification Search
USPC ................................ 600/30, 37; 606/151, 215
See application file for complete search history.

(56) References Cited

U.S. PATENT DOCUMENTS

| | | | |
|---|---|---|---|
| 7,175,591 B2* | 2/2007 | Kaladelfos | 600/37 |
| 7,351,197 B2* | 4/2008 | Montpetit et al. | 600/30 |
| 2001/0049467 A1* | 12/2001 | Lehe et al. | 600/30 |
| 2002/0183762 A1* | 12/2002 | Anderson et al. | 606/104 |
| 2003/0114866 A1* | 6/2003 | Ulmsten et al. | 606/151 |
| 2005/0234291 A1* | 10/2005 | Gingras | 600/30 |
| 2006/0130848 A1* | 6/2006 | Carey | 128/830 |
| 2006/0229596 A1* | 10/2006 | Weiser et al. | 606/37 |
| 2008/0167729 A1* | 7/2008 | Nelson et al. | 623/23.72 |

FOREIGN PATENT DOCUMENTS

| | | | |
|---|---|---|---|
| WO | 03/028585 A2 | 4/2003 | |
| WO | 03/096929 A1 | 11/2003 | |
| WO | 2004/045457 A1 | 6/2004 | |
| WO | WO 2004045457 A1 * | 6/2004 | A61F 2/02 |
| WO | 2007/066169 A1 | 6/2007 | |
| WO | WO 2007066169 A1 * | 6/2007 | A61F 2/08 |

OTHER PUBLICATIONS

International Search Report and Written Opinion for PCT Patent Application No. PCT/US2010/036407, mailed on Jul. 30, 2010, 15 pages.

* cited by examiner

*Primary Examiner* — Jacqueline Cheng
*Assistant Examiner* — Kaylee Wilson
(74) *Attorney, Agent, or Firm* — Brake Hughes Bellermann LLP

(57) ABSTRACT

An implant includes a support member having a first portion and a second portion. The support member is configured to be in contact with a wall of a vagina of a patient. The first portion defines apertures having a first size. The second portion defines at least one aperture having a second size. The second size is larger than the first size. The aperture having the second size is configured to be substantially aligned with a scar or an incision in the wall of the vagina. The second portion is configured to better prevent erosion of the wall of the vagina near the scar or incision than the first portion.

20 Claims, 8 Drawing Sheets

SYNTHETIC GRAFT FOR SOFT TISSUE REPAIR

CROSS REFERENCE TO RELATED APPLICATIONS

This application is a nonprovisional of, and claims priority to, U.S. Provisional Patent Application No. 61/183,654, filed on Jun. 3, 2009, entitled "SYNTHETIC GRAFT FOR SOFT TISSUE REPAIR," which is incorporated by reference herein in its entirety.

BACKGROUND

The invention relates generally to medical devices and more particularly to implants and methods for delivering implants within a pelvic region of a patient to treat various pelvic dysfunctions.

A variety of medical procedures are performed to treat various female pelvic dysfunctions, including procedures to treat urinary incontinence, and to correct various prolapse conditions such as uterine prolapse, cystoceles, rectoceles, and vaginal vault prolapse.

Women often experience vaginal prolapse due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina. It is relatively common for a hysterocele and cystocele or hysterocele and rectocele, or other combinations thereof to occur at the same time. It is also common for different types of prolapse to occur in relatively quick succession.

Treatment has included suturing procedures or the use of implants for support or suspension. For example, a hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Where an implant is exposed to a tissue, for example a wall of the vagina, tissue erosion and/or tissue shrinkage can occur. Further, sensitive vaginal tissue may become irritated by contact with an implant. Tissue erosion and irritation is greater when the implant is exposed to a scar created by an incision, for example a T-shaped scar created by a T-type incision during a vaginal hysterectomy. Tissue erosion can become severe and may require additional surgery. Accordingly, a need exists for an implant that reduces the amount of tissue erosion and irritation that occurs within a patient.

SUMMARY

An implant includes a support member having a first portion and a second portion. The support member is configured to be in contact with a wall of a vagina of a patient. The first portion defines apertures having a first size. The second portion defines at least one aperture having a second size. The second size is larger than the first size. The aperture having the second size is configured to be substantially aligned with a scar or an incision in the wall of the vagina. The second portion is configured to better prevent erosion of the wall of the vagina near the scar or incision than the first portion.

DETAILED DESCRIPTION

Figure 1:
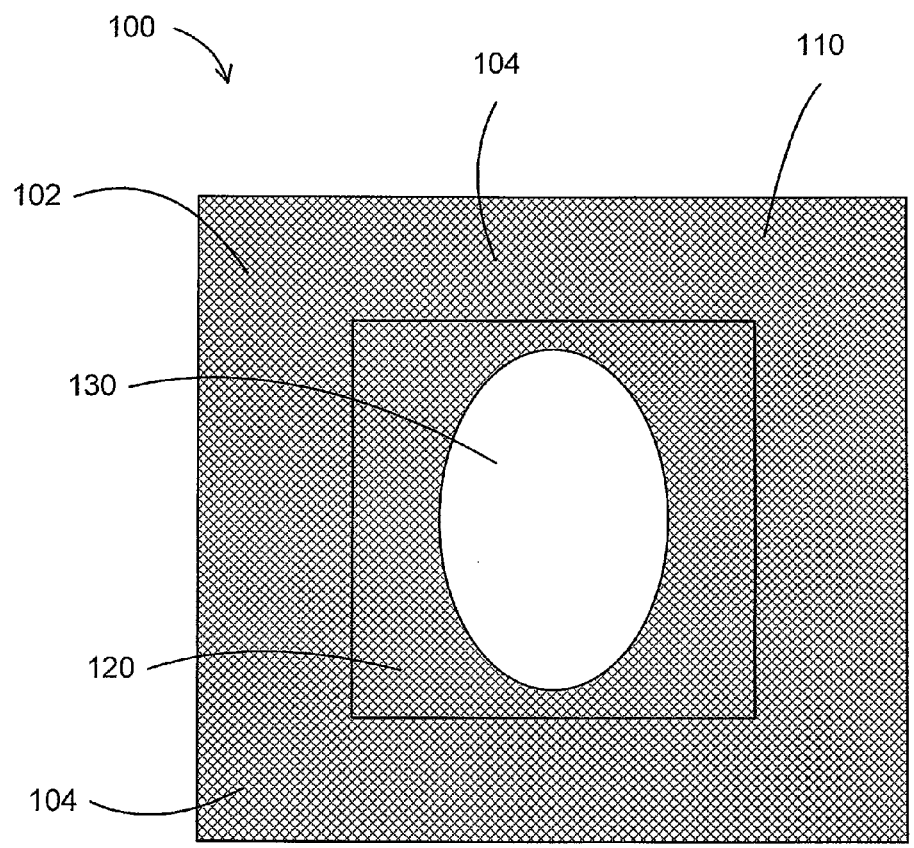
FIG. 1 is a schematic illustration of an implant, according to an embodiment.

In some embodiments, an implant includes a support member having a first portion and a second portion. The support member is configured to be in contact with a wall of a vagina of a patient. The first portion defines apertures having a first size. The second portion defines at least one aperture having a second size. The second size is larger than the first size. The aperture having the second size is configured to be substantially aligned with a scar or an incision in the wall of the vagina. The second portion is configured to better prevent erosion of the wall of the vagina near the scar or incision than the first portion. In some embodiments, the first portion is more dense than the second portion.

In some embodiments, a method of inserting an implant into a body of a patient includes making an incision in a portion of a body of a patient. An implant is inserted to support a tissue of the patient. The implant has a first portion and a second portion. The first portion defines apertures having a first size. In other embodiments, the first portion is a continuous sheet and does not define any apertures. The second portion defines at least one aperture having a second size. The second size is larger than the first size. The implant is positioned such that the at least one aperture having the second size is at least partially aligned with the incision such that at least a portion of the incision does not contact the implant. Said another way, the at least one aperture having the second size is configured to help prevent and/or reduce tissue erosion and/or tissue shrinkage of the tissue disposed within a region defined by a perimeter of the at least one aperture having the second size. The incision is then closed.

In some embodiments, a method of manufacturing an implant includes, knitting a mesh to include a first portion and a second portion. The mesh defines a first plurality of apertures and a second plurality of apertures larger than the first plurality of apertures. The first portion of the mesh includes apertures from the first plurality of apertures. The second portion of the mesh includes apertures from the second plurality of apertures. The second plurality of apertures are substantially positioned in a T-configuration configured to be aligned with a T-type incision used in a vaginal hysterectomy procedure.

In some embodiments, a method of manufacturing an implant includes, knitting a mesh to include a plurality of first apertures configured to promote tissue ingrowth and cutting the mesh to include at least one second aperture having a larger size than the first apertures. The at least one second aperture is configured to help prevent tissue erosion better than the first apertures.

As used herein, the term incision includes both open incisions and incisions that have been closed by, for example, means of a suture and/or the like. Accordingly, as used herein, the term incision includes any scars and/or scar tissue at the site of a closed incision.

FIG. 1 is a schematic illustration of an implant 100 according to an embodiment. The implant 100 includes a support member 102 having a first portion 110 and a second portion 120. The support member 102 is configured to be placed within a body of a patient and is configured to support a portion of the body. For example, the support member 102 can be similar to the grafts disclosed in U.S. Patent Application No. 61/017,257 entitled "Apparatus and Method for Uterine Preservation," filed on Dec. 28, 2007, which is hereby incorporated by reference in its entirety. For example, the support member 102 can be a variety of different shapes, sizes and configurations depending on the intended use for the particular implant. In some embodiments, the support member 102 can be substantially trapezoidal, rectangular, square, oval, or elliptical. The support member 102 can be shaped and sized to support a bladder (e.g., to treat a cystocele) and/or a bladder neck and/or to support a uterus (e.g., to treat a hysterocele), a rectum (e.g. to treat a rectocele), and/or a vagina.

The first portion 110 of the support member 102 can be formed with a mesh material to allow tissue in-growth to the implant 100 after implantation. In some embodiments, for example, the support member 102 can be a biocompatible mesh defining a plurality of apertures 104 each having a size greater than 500 microns. In other embodiments, each aperture of the plurality of apertures defined by the mesh can have a width less than 500 microns. In still other embodiments, each aperture of the plurality of apertures can have a width greater than 800 microns. In yet other embodiments, the first portion is a continuous sheet and does not define any apertures. In some embodiments, the first portion 110 of the support member 102 can be formed with a mesh material as described in U.S. Patent Pub. 2005/0038452 A1 to Chu, the disclosure of which is hereby incorporated by reference in its entirety. In some embodiments, the first portion 110 of the support member 102 can be formed with the Advantage® Mesh or the Polyform™ Synthetic Mesh material each provided by Boston Scientific Corporation. In other embodiments, the support member is formed with any other suitable biocompatible material.

Similar to the first portion 110 of the support member 102, the second portion 120 of the support member 102 can also be formed with a mesh material. In some embodiments, the first portion 110 of the support member 102 and the second portion 120 of the support member 102 are formed with the same material. In other embodiments, the first portion 110 of the support member 102 is formed with a different material than the second portion 120 of the support member 102. In some embodiments, the second portion 120 of the support member 102 is less dense than the first portion 120 of the support member 120.

The second portion 120 of the support member 102 defines an aperture 130. The aperture 130 can be any shape and have any position or orientation on the support member 102. The second portion 120 is configured to help prevent and/or reduce tissue erosion and/or tissue shrinkage of the tissue aligned with the aperture 130. Said another way, the second portion 120 is configured to help prevent and/or reduce tissue erosion and/or tissue shrinkage of the tissue disposed within a region defined by a perimeter of the aperture 130.

In some embodiments, the aperture 130 is specifically sized and positioned such that when positioned within the body of the patient, the aperture 130 is substantially aligned with a portion of the tissue that is especially prone to tissue erosion and/or tissue shrinkage. In some embodiments, the aperture 130 is configured to be at least partially aligned with an incision in the tissue of a patient. In such embodiments, the aperture 130 helps prevent and/or reduce tissue erosion and/or tissue shrinkage of the tissue located at the incision.

In some embodiments, the aperture 130 is circular, oval, square, triangular and/or any other suitable shape. In other embodiments, the second portion of the support member defines multiple apertures, as described in further detail herein. In some embodiments, the aperture 130 is in the center of the support member 102. In other embodiments, the aperture is offset from the center of the support member.

In some embodiments, the second portion 120 of the support member 102 also increases the flexibility of the support member 102. The second portion 120 includes only a small amount of mesh because of the aperture 130, thus increasing the flexibility of the support member 102.

In use, the implant 100 can be inserted into a body of a patient to support a portion of the body of the patient. In some embodiments, a delivery device is used to assist a medical practitioner in inserting the implant. In other embodiments, the medical practitioner does not use a delivery device during the insertion.

The support member 102 is positioned adjacent the tissue to be supported. For example, the support member 102 can be positioned to support a bladder (e.g., to treat a cystocele) and/or a bladder neck and/or support a uterus (e.g., to treat a hysterocele), a rectum (e.g. to treat a rectocele), and/or a vagina.

The aperture 130 is aligned with a portion of the tissue to be supported that is especially prone to tissue erosion. The aperture 130 is configured to help prevent and/or reduce tissue erosion and/or tissue shrinkage of the tissue with which it is aligned. Said another way, the aperture 130 helps prevent tissue erosion of the tissue disposed within a region defined by a perimeter of the aperture 130. In some embodiments, for example, the aperture 130 is aligned with an incision in the tissue, such as a T-type incision used in a vaginal hysterectomy. In such embodiments the aperture 130 can have T-shape and/or multiple apertures can form a T-shape. In other embodiments, the aperture is aligned with a portion of an adjacent tissue that is especially prone to tissue erosion. Said another way, the aperture can be aligned with a portion of a tissue that is not supported by the implant but will contact the implant because of its close proximity to the implant within the body of the patient. In some embodiments, the implant 100 is secured to the surrounding tissue using a suture, a strap, an anchor, and/or the like.

Figure 2:
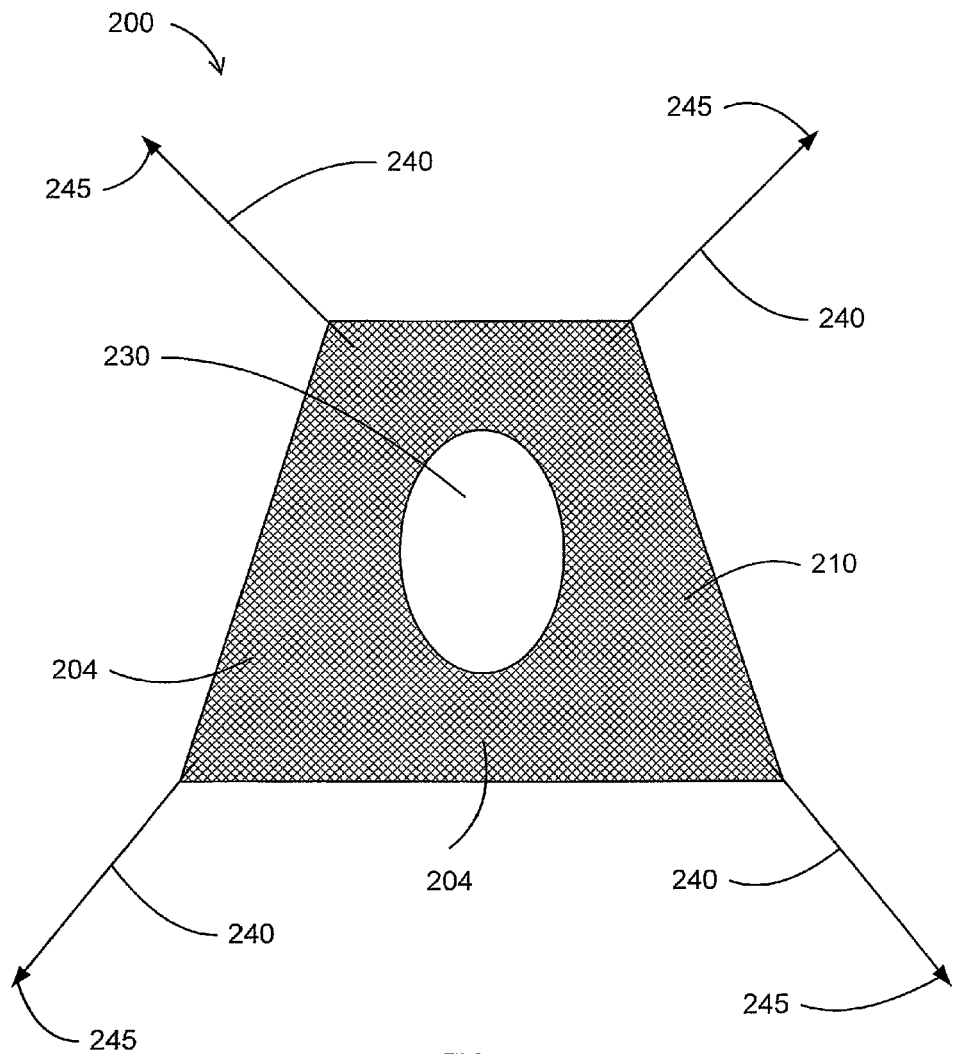
FIGS. 2-9 are illustrations of an implant, according to other embodiments.

FIG. 2 is an illustration of an implant 200, according to another embodiment. The implant 200 includes a support member 210, multiple sutures 240 and multiple needles or darts 245. While the support member 210 has a trapezoidal shape, in other embodiments, the support member can have any other shape suitable for its intended placement within the body. For example, the support member 210 can be rectangular, octagonal, hexagonal, elliptical and/or any other suitable shape. Further, similar to the support member 102, in some embodiments the support member 210 can be formed with a mesh material defining a plurality of apertures 204. In other embodiments, the support member is formed with any other suitable biocompatible material. In yet other embodiments, the first portion is a continuous sheet and does not define any apertures.

The support member 210 defines an aperture 230. The aperture 230 can be any shape and/or have any position on the support member 210 configured to help prevent and/or reduce tissue erosion and/or tissue shrinkage of the tissue aligned with the aperture. Said another way, the aperture 230 helps prevent and/or reduce tissue erosion and/or tissue shrinkage of the tissue disposed within a region defined by a perimeter of the aperture 230. In some embodiments, the aperture 230 is specifically sized and positioned such that when positioned within the body of the patient, the aperture 230 is substantially aligned with a portion of the tissue that is prone to tissue erosion and/or tissue shrinkage. In some embodiments, for example, the aperture 230 is configured to be at least partially aligned with an incision in the tissue of a patient. In such embodiments, the aperture 230 helps prevent and/or reduce tissue erosion and/or tissue shrinkage of the tissue located at and/or near the incision.

In some embodiments, the aperture 230 is circular, oval, square, triangular, rectangular and/or any other suitable shape. In other embodiments, the support member defines multiple apertures, as described in further detail herein. In some embodiments, the aperture 230 is in the center of the support member 210. In other embodiments, the aperture is offset from the center of the support member.

The sutures 240 are coupled to the support member 210 and are configured to aid in the insertion and/or retention of the support member 210 within a body of a patient, as further described in detail below. In some embodiments, the sutures 240 are constructed of a biocompatible reinforced structure. In some embodiments, for example, the sutures 240 can be 7×7 stainless steel braided wires. In such embodiments, the sutures 240 can also be coated with a polymer coating. A polymer coating can be used to help prevent breakage during the insertion processes and to prevent the braid from unraveling at its ends. The polymer coating also provides a smooth outer surface that minimizes the damage to tissue as the sutures 240 are inserted through the tissue. In other embodiments, the suture can be formed, for example, with a polymer and/or any other suitable material.

In other embodiments, implantable darts are coupled to the support member and are configured to aid in the insertion and/or retention of the support member within the body of the patient. In some embodiments, the implantable darts are polypropylene implantable darts. In other embodiments, the implantable darts are constructed of a bioresorbable polymer.

The sutures 240 can be coupled to the support member 210 by, for example, gluing, heat bonding, knotting, an interference fit, or other methods of attachment. In some embodiments, for example, a polymer coating of the sutures 240 is glued and/or heat bonded to the support member 210. In other embodiments, the suture can be knotted and/or crimped to the support member.

The darts 245 can be formed with various biocompatible materials, such as, for example, stainless steel, or other surgical steel. In some embodiments, the darts 245 are used to associate the implant 200 to a delivery device. The darts 245 are coupled to a distal end portion of the sutures 240 by any suitable means. In some embodiments, for example, the darts 245 are coupled to the sutures 240 by crimping, gluing and/or welding.

In use, the implant 200 can be inserted into a body of a patient to support a portion of the body of the patient. In some embodiments, a delivery device is used to assist a medical practitioner in inserting the implant. In other embodiments, the medical practitioner does not use a delivery device during the insertion.

The support member 210 is positioned adjacent the tissue to be supported. For example, the support member 210 can be positioned to support a bladder (e.g., to treat a cystocele) and/or a bladder neck and/or to support a uterus (e.g., to treat a hysterocele), a rectum (e.g. to treat a rectocele), and/or a vagina.

The aperture 230 is aligned with a portion of the tissue to be supported that is prone to tissue erosion. The aperture 230 is configured to help prevent and/or reduce tissue erosion and/or tissue shrinkage of the tissue with which it is aligned. Said another way, the aperture 230 helps prevent tissue erosion of the tissue disposed within a region defined by a perimeter of the aperture 230. In some embodiments, for example, the aperture 230 is aligned with an incision in the tissue, such as a T-type incision used in a vaginal hysterectomy. In such embodiments the aperture can have a T-shape and/or multiple apertures can form a T-shape. In other embodiments, the aperture is aligned with a portion of an adjacent tissue that is prone to tissue erosion. Said another way, the aperture can be aligned with a portion of a tissue that is not supported by the implant but will contact the implant because of its close proximity to the implant within the body of the patient.

The darts 245 and the sutures 240 are used to insert and secure the support member 210 in its position adjacent the tissue to be supported. The darts 245 can be used to pierce and/or dilate an anchoring site in a tissue in close proximity to the tissue to be supported. Distal end portions of the sutures 240 are then passed through the anchoring site. In some embodiments, the distal end portions of the sutures 240 can be coupled to the proximal end portion of the sutures 240 or the support member 210. In such embodiments, the sutures 240 form loops that extend through the anchoring site within the tissue and support the support member 210 of the implant 200. In other embodiments, the sutures include barbs, tissue anchors, and/or other suitable devices that allow movement through the tissue in a first direction but restrict movement of the suture through the tissue in a second direction opposite the first direction. In such embodiments, the barbs and/or tissue anchors help support the support member.

Figure 3:
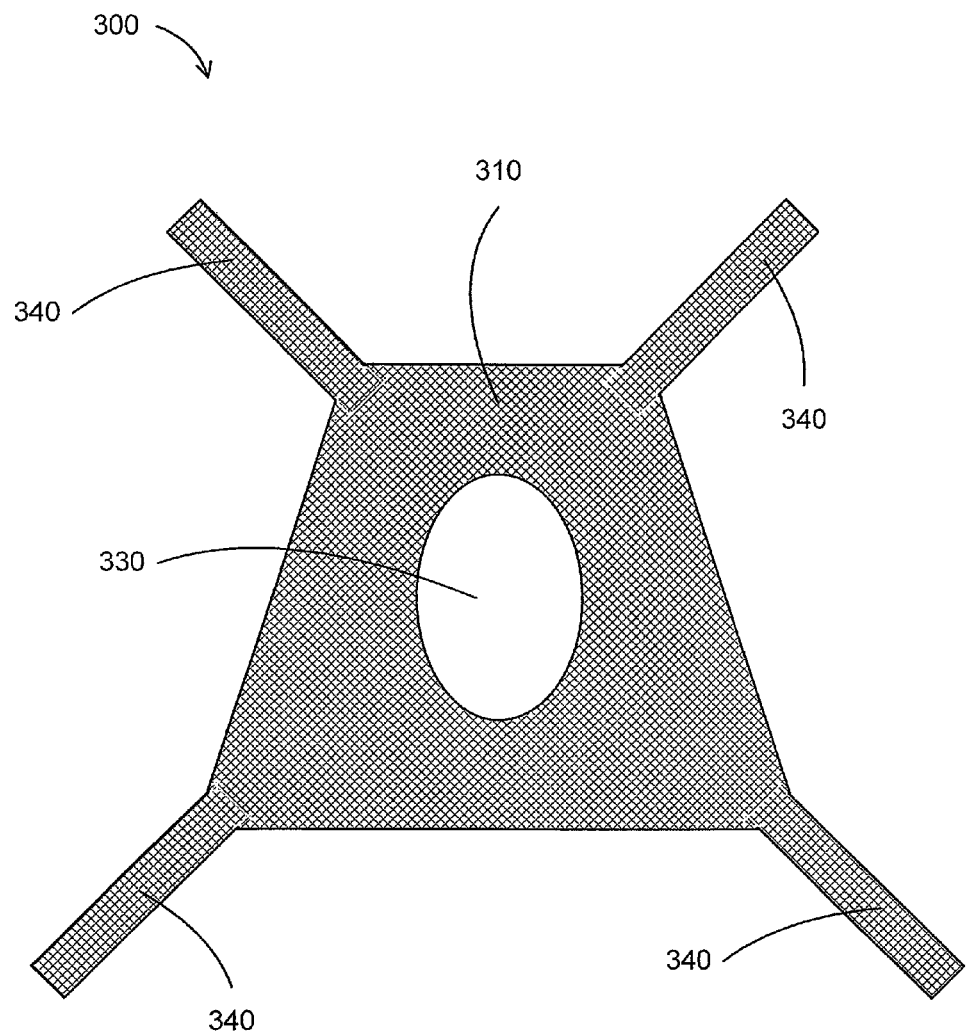

While the implant 200 uses multiple sutures 240 to insert and support the support member 210, FIG. 3 is an illustration of an implant 300 that uses multiple straps 340 to support a support member 310. The implant 300 includes a support member 310 that defines an aperture 330. The support member 310 and the aperture 330 are structurally and functionally similar to the support member 210 and aperture 230 of the implant 200, respectfully.

The straps 340 of the implant 300 are can be formed with a mesh material to allow tissue in-growth after implantation. In some embodiments, for example, the straps 340 can be formed with a mesh material similar to the mesh material described above with respect to the support member 102 of the implant 100. In some embodiments, the straps are formed with the same material as the support member 310. In other embodiments, the straps are formed with a different material than the support member.

The straps 340 of the implant 300 are coupled to the support member 310 of the implant 300. In some embodiments, the straps 340 are monolithically formed with the support member 310. In other embodiments, the straps are coupled to the support member by gluing, heat bonding, and/or other suitable method of attachment.

In some embodiments, the straps 340 of the implant 300 include tangled portions (not shown in FIG. 3). The tangled portions are roughened or jagged edges or areas, such as can result from cutting a woven or knit mesh material. The tangled portion can be used, for example, to anchor or secure the implant 300 to tissue.

In some embodiments, delivery aids, such as sleeves (not shown in FIG. 3) are disposed over the straps 340. The delivery aids can be included as part of an implant (e.g., provided to a physician assembled) or can be coupled to or associated with an implant just prior to implantation. Such delivery aids are typically removed after placing the straps 340 of the implant 300 at a desired tissue securement location, leaving the straps 340 to engage the tissue and support the support member 310 of the implant 300. In some embodiments, for example, a sleeve assembly can be used to lead the straps 340 of the implant 300 through a tissue of a patient. The sleeve assembly can be used such that the tangled portions of the straps 340 do not engage the tissue before they are properly located within the tissue.

In use, the implant 300 can be inserted into a body of a patient to support a portion of the body of the patient. In some embodiments, a delivery device is used to assist a medical practitioner in inserting the implant 300. In other embodiments, the medical practitioner does not use a delivery device during the insertion.

The support member 310 is positioned adjacent the tissue to be supported. For example, the support member 310 can be positioned to support a bladder (e.g., to treat a cystocele) and/or a bladder neck and/or to support a uterus (e.g., to treat a hysterocele), a rectum (e.g. to treat a rectocele), and/or a vagina.

The aperture 330 is aligned with a portion of the tissue to be supported that is prone to tissue erosion. The aperture 330 is configured to help prevent and/or reduce tissue erosion and/or tissue shrinkage of the tissue with which it is aligned. Said another way, the aperture 330 helps prevent tissue erosion of the tissue disposed within a region defined by a perimeter of the aperture 330. In some embodiments, for example, the aperture 330 is aligned with an incision in the tissue, such as a T-type incision used in a vaginal hysterectomy. In such embodiments the aperture can have a T-shape and/or multiple apertures can form a T-shape. In some embodiments, for example, the aperture 330 is aligned with an incision in the tissue, such as T-type incision used in a vaginal hysterectomy. The aperture 330 helps prevent and/or reduce tissue erosion and/or tissue shrinkage of the tissue with which it is aligned. In other embodiments, the aperture is aligned with a portion of an adjacent tissue that is prone to tissue erosion. Said another way, the aperture can be aligned with a portion of a tissue that is not supported by the implant but will contact the implant because of its close proximity to the implant within the body of the patient.

The straps 340 are inserted into anchoring sites in tissue that are in close proximity to the tissue to be supported. In some embodiments, sleeve assemblies can be used to assist the medical practitioner in inserting the straps 340 into the anchoring sites. In such embodiments, once the straps are correctly positioned within the anchoring sites, the sleeve assemblies can be removed from the straps. Once inserted into the anchoring sites, the tangled portions of the straps 340 engage the surrounding tissue and prevent movement of the straps in a proximal direction. In such a manner, the straps 340 support the support member 310 of the implant.

FIGS. 4-8 show various support members of implants defining apertures of different shapes, sizes and configurations. The support members shown in FIGS. 4-8 are shown as being trapezoidal in shape. In other embodiments, the support members can be any other shape, such as, for example, rectangular, square, oval, or elliptical. The apertures of the support members shown in FIGS. 4-8 are shown by way of example. In other embodiments, the apertures can have any shape, orientation and/or configuration that aligns with tissue that is prone to erosion and/or tissue that should not contact the support member.

Figure 4:
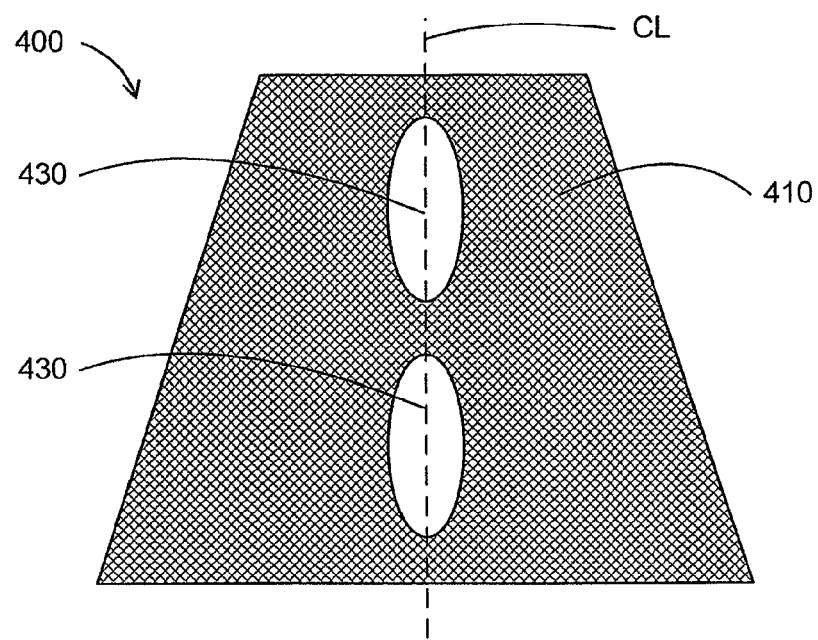

FIG. 4 shows an implant 400 having a support member 410 with a first portion and a second portion that is less dense than the first portion. The second portion defines two oval shaped apertures 430. The apertures 430 are substantially aligned along a center line CL defined by the support member 410. In some embodiments, an incision in a tissue, such as a vagina, can be substantially aligned with the apertures 430 when the implant 400 is inserted into a body of a patient. In such embodiments, the incision can be a longitudinal incision on the center line of the vagina. In other embodiments, other tissue prone to erosion can be aligned with the apertures. The mesh between the two apertures 430 provides some support to the portion of the tissue along the center line CL.

Figure 5:
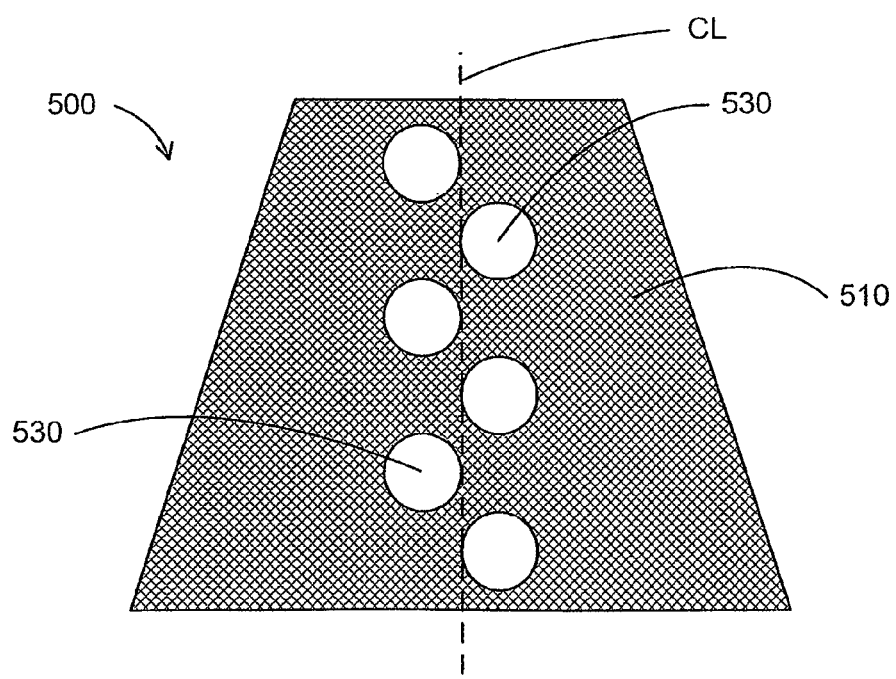

FIG. 5 shows an implant 500 having a support member 510 defining multiple circular apertures 530. In such embodiments, because more mesh is between the apertures 530 than in the implant 400, more support may be provided to the portion of the tissue along a center line CL defined by the support member 510.

Figure 6:
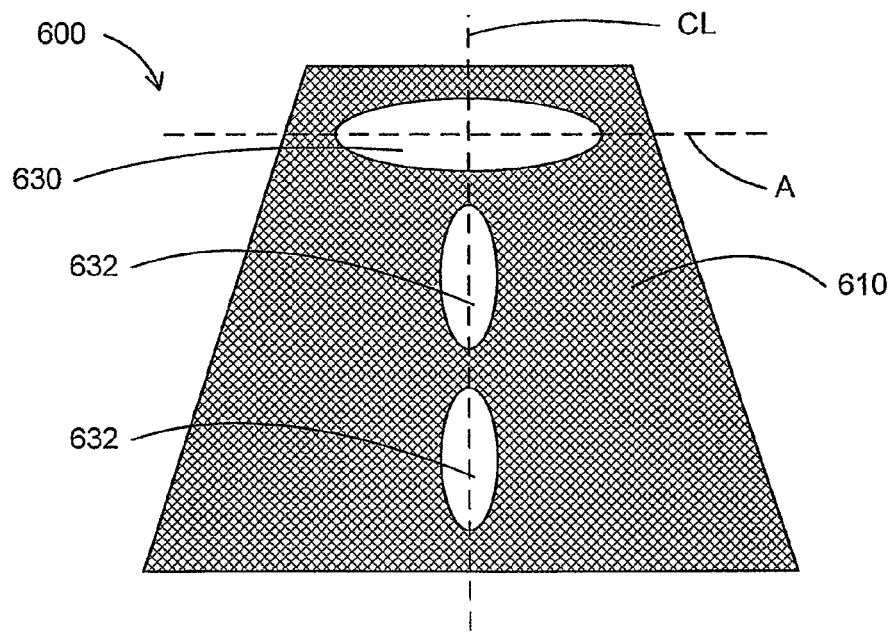

FIG. 6 shows an implant 600 having a support member 610 defining two oval shaped apertures 632 aligned along a center line CL defined by the support member 610 and a third oval shaped aperture 630 that defines an axis A that is substantially perpendicular to the center line CL. The axis A defined by the third aperture 630 defines a T-shape with the center line CL. Accordingly, the apertures 630, 632 substantially form a T-shape. This T-shape is configured to be aligned with a T-type incision used in a vaginal hysterectomy procedure. In such embodiments, the T-type incision, which is prone to tissue erosion, minimally contacts the material or mesh of the support member 610, reducing the chance of erosion.

Figure 7:
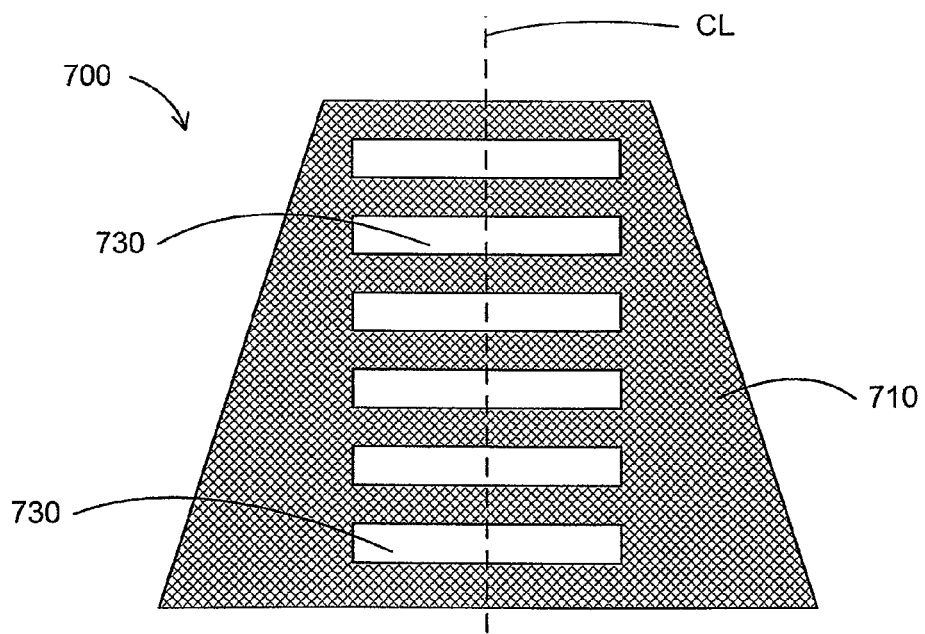
Figure 8:
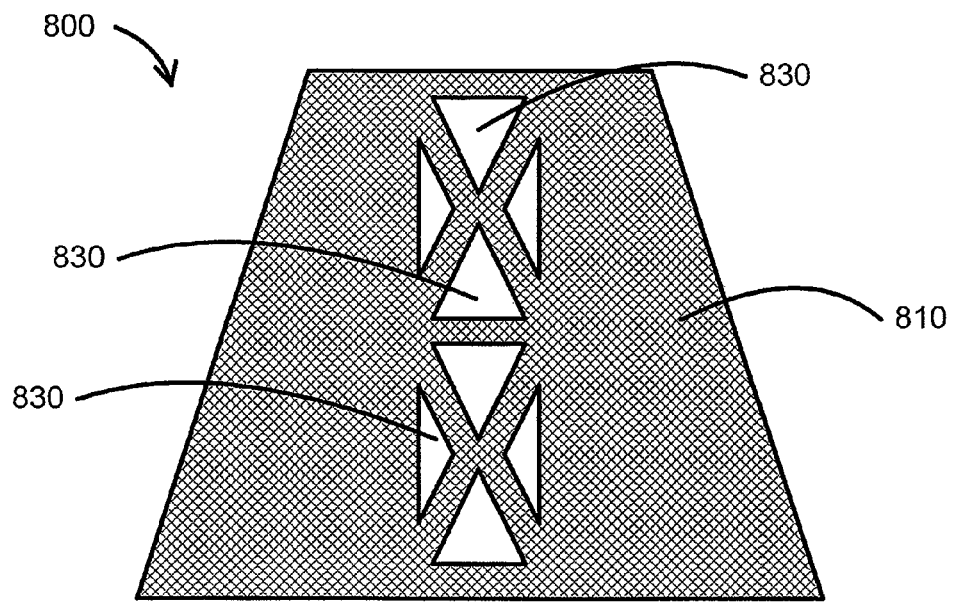

The implants 700, 800 in FIGS. 7 and 8, respectively, show examples of other configurations of sizes and shapes of apertures that can be used. For example, FIG. 7 shows an implant 700 having a support member 710 defining multiple rectangular shaped apertures 730 defining axes substantially perpendicular to a center line CL defined by the support member 710. FIG. 8 shows an implant 800 having a support member 810 defining multiple triangular shaped apertures 830. Similar to the embodiments described above, in some embodiments, the rectangular shaped apertures 730 (FIG. 7) and the triangular shaped apertures 830 (FIG. 8) can be substantially aligned with an incision or other sensitive tissue to minimize the contact that the implants 700, 800 have with the incision or other sensitive tissue. In such embodiments, the incision can be a longitudinal incision on the center line of the vagina.

Figure 9:
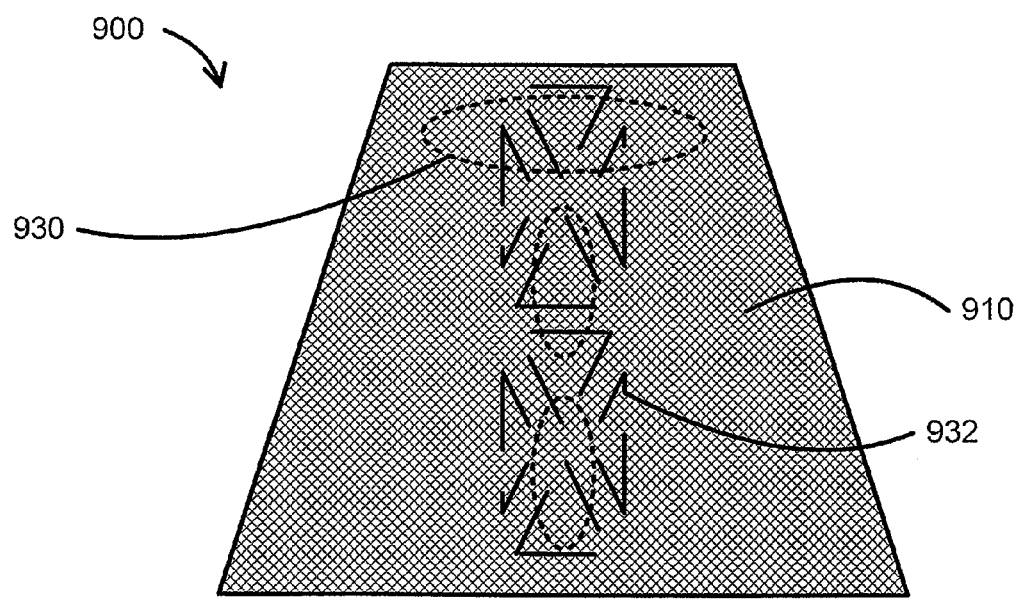

FIG. 9 shows an implant 900 having a support member 910 with oval outlines 930 rather than the apertures 630, 632 of FIG. 6 and triangular outlines 932 rather than the apertures 830 of FIG. 8. To create apertures within the support member 910, the medical practitioner can cut along the outlines of the desired apertures (either 930 or 932). In other embodiments, the outlines are perforated such that the medical practitioner can punch out the desired apertures.

The outlines 930, 932 allow a medical practitioner to choose which configuration of apertures is most effective for a particular patient. For example, if the patient had a vaginal hysterectomy using a T-type incision, the medical practitioner might want to define apertures similar to those in FIG. 6. Accordingly, the medical practitioner can cut along the outline 930 to define these apertures. Such outlines 930, 932 allow a physician to decide the best shape, size and configuration of the apertures.

Figure 10:
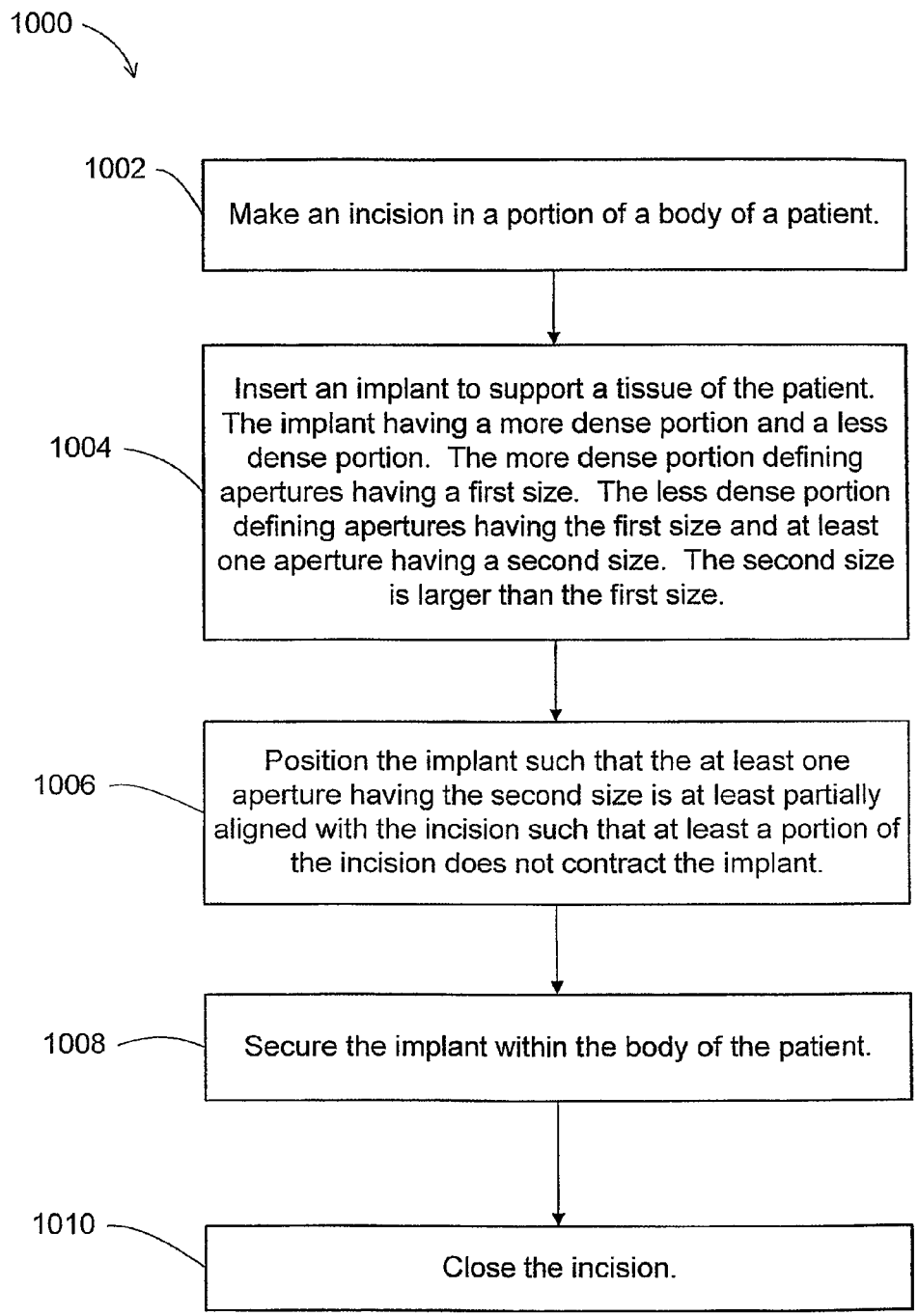
FIG. 10 is a flow chart illustrating a method of inserting an implant within a body of a patient, according to an embodiment.

FIG. 10 is a flow chart illustrating a method 1000 of inserting an implant within a body of a patient, according to an embodiment. The method 1000 includes making an incision in a portion of a body of a patient, at 1002. In some embodiments, the incision can be made, for example, in a vagina of a patient and/or another tissue within the pelvic region of the patient. In other embodiments, the incision is made in another portion of the body of the patient.

An implant is inserted to support a tissue of the patient, at 1004. The implant has a first portion and a second portion. The first portion defines apertures having a first size. In other embodiments, the first portion is a continuous sheet and does not define any apertures. The second portion defines apertures having the first size and at least one aperture having a second size. The second size is larger than the first size. In some embodiments, the tissue to be supported is on the portion of the body where the incision was made. In other embodiments, the tissue to be supported is in close proximity to the portion of the body where the incision was made.

The implant is positioned such that the at least one aperture having the second size is at least partially aligned with the incision such that at least a portion of the incision does not contact the implant, at 1006. This reduces the chance of tissue erosion occurring at the site of the incision.

The implant is then secured within the body of the patient. In some embodiments, at least one strap of the implant is inserted into a tissue in close proximity to the portion of the body of the patient, at 1008. In other embodiments, a suture is used to secure the implant rather than a strap. The incision is then closed, at 1010.

Figure 11:
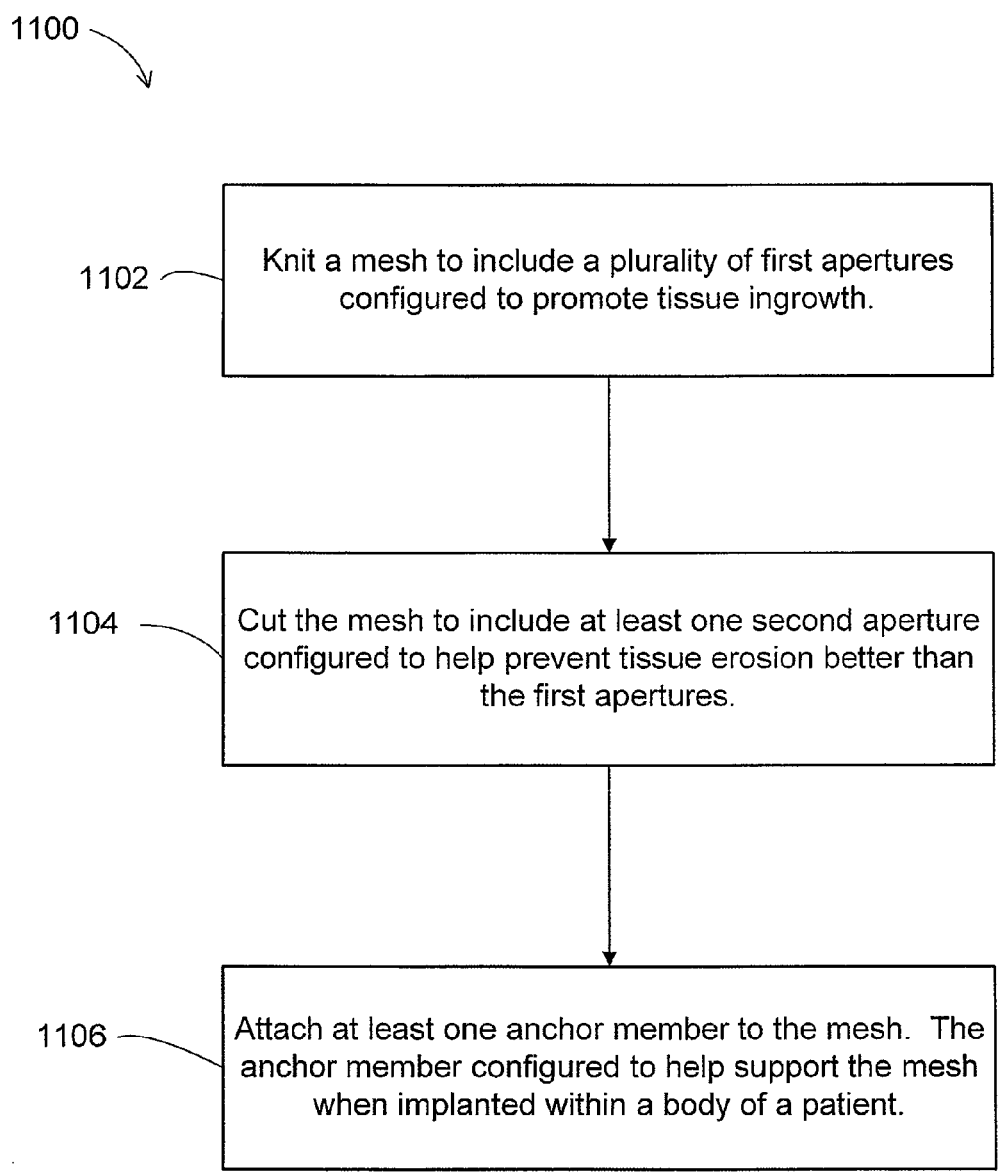
FIG. 11 is a flow chart illustrating a method of manufacturing an implant, according to an embodiment.

FIG. 11 is a flow chart illustrating a method 1100 of manufacturing an implant, according to an embodiment. The method 1100 includes knitting a mesh to include a plurality of first apertures configured to promote tissue ingrowth, at 1102. The mesh can be configured to support a portion of a body of a patient when implanted within the body of the patient.

The mesh is then cut to include at least one second aperture configured to help prevent and/or reduce tissue erosion and/or tissue shrinkage better than the first apertures, at 1104. The second aperture is configured to be aligned with a portion of a tissue of the patient that is prone to tissue erosion when the mesh is implanted within the body of the patient. In some embodiments, the portion of the tissue prone to tissue erosion is on the portion of the body of the patient configured to be supported by the mesh. In other embodiments, the portion of the tissue prone to tissue erosion is in close proximity to the portion of the body to be supported by the mesh.

At least one anchor member is attached to the mesh, at 1106. The anchor member is configured to help support the mesh when implanted within the body of the patient. In some embodiments, the anchor member is a suture. In other embodiments, the anchor member is a strap coupled to the mesh or knitted as a portion of the mesh.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, any of the above described implants can include any shape, size, and/or configuration of apertures. Further, any of the above described implants can include straps, sutures, tissue anchors, and/or anything else configured to secure the implant to the surrounding tissue.

In some embodiments, an implant includes a support member having a first portion and a second portion. The support member is configured to be in contact with a wall of a vagina of a patient. The first portion defines apertures having a first size. The second portion defines apertures having the first size and an aperture having a second size. The second size is larger than the first size. The aperture having the second size is configured to be substantially aligned with an incision within the wall of the vagina. The second portion is configured to better reduce erosion of the wall of the vagina than the first portion.

In some embodiments, the aperture having the second size is substantially oval in shape. In some embodiments, the aperture having the second size is configured to be aligned with at least a portion of a T-type incision in the wall of the vagina used in a vaginal hysterectomy procedure. In some embodiments, the support member is constructed of a synthetic mesh.

In some embodiments, a portion of the wall of the vagina substantially aligned with the aperture having the second size includes an incision. In some embodiments, the aperture having the second size is aligned along a center line of the support member. In some embodiments, the support member is constructed of a polypropylene mesh.

In some embodiments, the aperture having the second size has a shape that is substantially similar to at least a portion of a shape of the incision. In some embodiments, the implant further includes a strap configured to be inserted into a tissue of the patient to support the support member within a body of the patient.

In some embodiments, the second portion defines an aperture having a third size. The aperture having the second size defines a longitudinal axis. The aperture having the third size defines a longitudinal axis substantially perpendicular to the longitudinal axis defined by aperture having the second size.

In some embodiments, the second portion defines an aperture having a third size. The aperture having the second size defines a longitudinal axis and is configured to be substantially aligned with a first portion of a T-type incision in the wall of the vagina used in a vaginal hysterectomy procedure. The aperture having the third size defines a longitudinal axis and is configured to be substantially aligned with a second portion of the T-type incision. The longitudinal axis defined by the aperture having the second size is substantially perpendicular to the longitudinal axis defined by the aperture having the third size.

In some embodiments, the apertures having the first size encourage tissue ingrowth better than the aperture having the second size. In some embodiments, the support member is configured to support the vagina of the patient. In some embodiments, the aperture having the second size is a first aperture having the second size, the second portion defines a plurality of apertures having the second size, the plurality of apertures being substantially triangular in shape.

In some embodiments, the aperture having the second size is a first aperture having the second size and the second portion defines a plurality of apertures having the second size. The plurality of apertures are substantially circular in shape.

In some embodiments, the aperture having the second size is a first aperture having the second size. The second portion defines a plurality of apertures having the second size. The plurality of apertures are substantially aligned along a center line of the support member.

In some embodiments, a method includes making an incision in a portion of a body of a patient. An implant is inserted to support a tissue of the patient. The implant has a first portion and a second portion. The first portion defines apertures having a first size. The second portion defines apertures having the first size and at least one aperture having a second size. The second size is larger than the first size. The implant is positioned within the body of the patient such that the at least one aperture having the second size is at least partially aligned with the incision such that at least a portion of the incision does not contact the implant. The incision is then closed.

In some embodiments, the making the incision includes making a T-type incision in the wall of the vagina used in a vaginal hysterectomy procedure. In some embodiments, the incision is closed using a suture. In some embodiments, the method further includes the step of securing the implant within the body of the patient by inserting at least one strap of the implant into a second tissue of the body of the patient.

In some embodiments, the at least one aperture having the second size has a shape that is substantially similar to a shape of the incision. The inserting includes aligning at least a portion of the at least one aperture having the second size with at least a portion of the incision. In some embodiments, the incision is made in a vagina of the patient. In some embodiments, the inserting the implant includes inserting an implant constructed of a synthetic mesh.

In some embodiments, a method of manufacturing an implant includes knifing a mesh to include a first portion and a second portion. The mesh defining a first plurality of apertures and a second plurality of apertures larger than the first plurality of apertures. The first portion includes apertures from the first plurality of apertures. The second portion includes apertures from the second plurality of apertures. The second plurality of apertures are substantially positioned in a T-configuration.

In some embodiments, the second portion includes apertures from the first plurality of apertures. In some embodiments, the second portion is configured to help prevent erosion of a tissue better than the first portion. In some embodiments, the method further includes attaching at least one suture to the mesh. The suture is configured to help support the mesh when implanted within a body of a patient. In some embodiments, the second plurality of apertures are configured to be aligned with a T-type incision in the wall of the vagina used in a vaginal hysterectomy procedure.

In some embodiments, a method of manufacturing an implant includes knifing a mesh to include a plurality of first apertures configured to promote tissue ingrowth and cutting the mesh to include at least one second aperture. The at least one second aperture is configured to help prevent tissue erosion and/or shrinkage better than the first apertures.

In some embodiments, the cutting includes cutting the at least one second aperture such that the at least one second aperture has a shape substantially similar to the shape of an incision. In some embodiments, the first apertures promote tissue ingrowth better than the at least one second aperture.

In some embodiments, the method further includes attaching at least one suture to the mesh. The suture is configured to help support the mesh when implanted within a body of a patient. In some embodiments, the cutting the mesh includes cutting the at least one aperture in a T-shape. The at least one second aperture is configured to be aligned with a T-type incision in the wall of the vagina used in a vaginal hysterectomy procedure.

In some embodiments, the cutting of the mesh includes cutting a second aperture. The first aperture defines a longitudinal axis substantially perpendicular to a longitudinal axis defined by the second aperture such that the first aperture and the second aperture are configured to be aligned with a T-type incision in the wall of the vagina used in a vaginal hysterectomy procedure.

What is claimed is:

1. An implant, comprising:
   a support member having a first portion and a second portion, the first portion being formed of a first mesh material, the second portion being formed of a second mesh material, the second mesh material being less dense than the first mesh material, the support member configured to be in contact with a wall of a vagina of a patient, the first portion defining a plurality of apertures having a first size, the second portion defining a plurality of apertures having a second size, a first aperture having a third size, and a second aperture having a fourth size, the second size being larger than the first size, the third size being larger than the first size and the second size, the fourth size being larger than the first size and the second size, the first aperture and the second aperture collectively forming a "T" shape and being configured to be aligned with an incision within the wall of the vagina, the first aperture being defined by a first perforated outline in the second mesh material and the second aperture being defined by a second perforated outline in the second mesh material.

2. The implant of claim 1, wherein the first aperture is substantially oval in shape.

3. The implant of claim 1, wherein the first aperture and the second aperture are configured to be aligned with at least a portion of a T-type incision in the wall of the vagina used in a vaginal hysterectomy procedure.

4. The implant of claim 1, wherein the first portion of the support member includes a first synthetic mesh and the second portion of the support member includes a second synthetic mesh.

5. The implant of claim 1, wherein the first aperture is aligned along a center line of the support member.

6. The implant of claim 1, wherein the first portion of the support member includes a first polypropylene mesh and the second portion of the support member includes a second polypropylene mesh.

7. The implant of claim 1, wherein the first aperture and the second aperture collectively have a shape that is similar to at least a portion of a shape of the incision.

8. The implant of claim 1, further comprising:
   a strap configured to be inserted into a tissue of the patient to support the support member within a body of the patient.

9. The implant of claim 1, wherein the fourth size is larger than the third size, the first aperture defining a longitudinal axis, the second aperture defining a longitudinal axis perpendicular to the longitudinal axis defined by the first aperture.

10. The implant of claim 1, wherein the first aperture defines a longitudinal axis and is configured to be substantially aligned with a first portion of a T-type incision in the wall of the vagina used in a vaginal hysterectomy procedure, the second aperture defines a longitudinal axis and is configured to be substantially aligned with a second portion of the T-type incision, the longitudinal axis defined by the first aperture being perpendicular to the longitudinal axis defined by the second aperture.

11. The implant of claim 1, wherein the first aperture is circular in shape.

12. The implant of claim 1, wherein the second portion of the support member defines a third aperture, the first aperture and the third aperture being aligned along a center line of the support member.

13. The implant of claim 1, further comprising:
a suture having a first end portion coupled to the support member and a second end portion coupled to a needle member.

14. The implant of claim 1, further comprising:
a strap member coupled to and extending from the support member, the strap member being formed from the first mesh material.

15. A method, comprising:
making an incision in a body of a patient;
defining a first aperture in an implant by removing a first perforated outline in the implant;
defining a second aperture in the implant by removing a second perforated outline in the implant;
inserting the implant to support a tissue of the patient;
positioning the implant within the body of the patient, the positioning including at least partially aligning the first aperture with a first portion of the incision and at least partially aligning the second aperture with a second portion of the incision; and
closing the incision.

16. The method of claim 15, wherein:
making the incision includes making a T-type incision in a wall of a vagina of the patient in a vaginal hysterectomy procedure, the first portion of the incision is a first portion of the T-type incision and the second portion of the incision is a second portion of the T-type incision, and the first aperture and the second aperture collectively form a T-shape in the implant.

17. The method of claim 15, wherein the tissue of the body of the patient is a first tissue of the body of the patient, the method further comprising:
securing the implant within the body of the patient by inserting at least one strap of the implant into a second tissue of the body of the patient.

18. A method of manufacturing an implant, comprising:
knitting a mesh to include a first portion and a second portion, the first portion of the mesh being formed of a first mesh material, the second portion of the mesh being formed of a second mesh material that is different than the first mesh material, the mesh defining a first plurality of apertures and a second plurality of apertures, the second plurality of apertures having a size that is larger than a size of the first plurality of apertures, the first portion including apertures from the first plurality of apertures, the second portion including apertures from the second plurality of apertures, the second portion further including:
a first perforated outline defining a first aperture having a size that is larger than the size of the first plurality of apertures and that is larger than the size of the second plurality of apertures; and
a second perforated outline defining a second aperture having a size that is larger than the size of the first plurality of apertures and that is larger than the size of the second plurality of apertures,
the first aperture and the second aperture being substantially arranged in a T-shape and configured to be aligned with a T-type incision.

19. The method of claim 18, wherein the second portion further includes apertures from the first plurality of apertures.

20. The method of claim 18, further comprising:
attaching at least one suture to the mesh, the suture being configured to help support the mesh when implanted within a body of a patient.

* * * * *